United States Patent [19]

Dominianni et al.

[11] 4,131,656

[45] Dec. 26, 1978

[54] INTERMEDIATES FOR 5-(TERTIARY ALKYL) RESORCINOL PREPARATION

[75] Inventors: Samuel J. Dominianni; Charles W. Ryan, both of Indianapolis, Ind.

[73] Assignee: Eli Lilly and Company, Indianapolis, Ind.

[21] Appl. No.: 874,183

[22] Filed: Feb. 1, 1978

Related U.S. Application Data

[62] Division of Ser. No. 695,674, Jun. 14, 1976, Pat. No. 4,087,410.

[51] Int. Cl.$^2$ .............................................. C07F 9/02
[52] U.S. Cl. ...................................... 260/951; 260/937
[58] Field of Search ................................ 260/937, 951

[56] References Cited

U.S. PATENT DOCUMENTS 3,107,164   10/1963   Szabo et al. ..................... 260/951

*Primary Examiner*—Elbert L. Roberts
*Assistant Examiner*—Robert C. Whittenbaugh
*Attorney, Agent, or Firm*—Charles W. Ashbrook; Everet F. Smith

[57] ABSTRACT

2,6-Dimethoxyphenol reacts with a tertiary carbinol in the presence of an acid to provide exclusively a 1-hydroxy-2,6-dimethoxy-4-(tertiary alkyl)benzene, which when reacted with a halogenated disubstituted phosphite affords a 2,6-dimethoxy-4-(tertiary alkyl)phenyl disubstituted phosphate. Reduction of the phenyl phosphate derivative by reaction with an alkali metal affords a 1-(tertiary alkyl)-3,5-dimethoxybenzene, which upon reaction with a demethylating agent provides a 5-(tertiary alkyl)resorcinol.

10 Claims, No Drawings

INTERMEDIATES FOR 5-(TERTIARY ALKYL) RESORCINOL PREPARATION

This is a division, of application Ser. No. 695,674, filed June 14, 1976, now U.S. Pat. No. 4,087,410.

BACKGROUND OF THE INVENTION

A number of 5-alkyl resorcinols are known. Such compounds have a variety of utilities, including that of being important starting materials in the synthesis of 1-hydroxy-3-alkyl-dibenzopyran derivatives. Adams et al. discovered that the biological activity of such dibenzopyran derivatives could be increased by introducing branching at the 1'-position of the 3-alkyl moiety, see J. Am. Chem. Soc. Vol. 70, 664 (1948). It accordingly became necessary to prepare 5-(tertiary alkyl)resorcinols which could be used in the preparation of such dibenzopyrans having highly branched side-chains in the 3-position. The synthesis of 5-(tertiary alkyl)resorcinols was particularly difficult, as demonstrated by the process disclosed by Adams et al., ibid. Such process included the conversion of 3,5-dimethoxybenzoic acid to 3,5-dimethoxybenzaldehyde, which upon reduction afforded 3,5-dimethoxybenzyl alcohol. Chlorination afforded 3,5-dimethoxybenzyl chloride, which was then converted to 3,5-dimethoxybenzyl cyanide. Dialkylation of this latter compound provided 3,5-dimethoxy-α,α-dimethylbenzyl cyanide, which when reacted with n-pentyl magnesium bromide afforded 3,5-dimethoxy-(1,1-dimethyl-2-oxoheptyl)-benzene. Reduction of this latter named compound provided the corresponding alcohol which was next dehydrated to the corresponding alkene, and finally reduction of such alkene afforded 3,5-dimethoxy-(1,1-dimethylheptyl)benzene. Demethylation of the latter compound afforded the desired resorcinol.

It is clear from the foregoing that such processes for preparing resorcinol intermediates are unattractive from a commercial standpoint due to the length of the overall process and cost of starting materials. Very little developmental work has been attempted with Adam's process in an effort to simplify that process or to devise a better process for preparing 5-(tertiary alkyl)resorcinols. An object of this invention is to provide a simple and efficient process for preparing 5-(tertiary alkyl)-resorcinols. It has now been discovered that 2,6-dimethoxyphenol surprisingly is alkylated almost exclusively at the 4-position by reaction with a tertiary carbinol in the presence of an acid. Such alkylation provides a 1-hydroxy-2,6-dimethoxy-4-(tertiary alkyl)benzene which can readily be converted to a 5-(tertiary alkyl)-resorcinol. Such process affords high yields of the desired 5-(tertiary alkyl)resorcinol in only four steps, and starting from relatively inexpensive starting materials.

SUMMARY OF THE INVENTION

This invention relates to the preparation of 5-(tertiary alkyl)resorcinols from 2,6-dimethoxyphenol, and to intermediates useful in such process. More particularly, the invention provides a process for preparing a compound of the formula

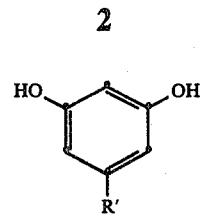

wherein $R_1$ is adamantyl or $-CR_2R_3R_4$, in which $R_2$ and $R_3$ independently are $C_1-C_6$ alkyl, and $R_4$ is $C_1-C_6$ alkyl, phenyl, cyclohexyl or adamantyl; which process comprises reacting 2,6-dimethoxyphenol with a tertiary carbinol of the formula $R_1OH$ in the presence of an acid to provide a compound of the formula

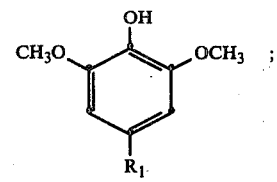

reacting such 1-hydroxy-2,6-dimethoxy-4-(tertiary alkyl)benzene with a halogenated disubstituted phosphite to provide the corresponding 2,6-dimethoxy-4-(tertiary alkyl)phenyl disubstituted phosphate; reacting such 2,6-dimethoxy-4-(tertiary alkyl)phenyl disubstituted phosphate with an alkali metal to provide a 1-(tertiary alkyl)-3,5-dimethoxybenzene of the formula

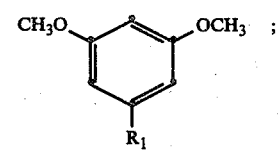

and reacting the 1-(tertiary alkyl)-3,5-dimethoxybenzene with a demethylating agent such as pyrindinium chloride, a boron trihalide or an aluminum trihalide, or hydrobromic acid in acetic acid, to effect cleavage of the two methyl ether groups and thus provide the desired resorcinol derivative.

The invention additionally provides new compounds which are useful as intermediates in the preparation of 5-(tertiary alkyl)resorcinols. Such compounds have the formula

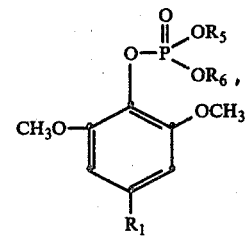

wherein $R_1$ has the above defined meaning, $R_5$ and $R_6$ independently are $C_1-C_3$ alkyl or phenyl, or taken together are ethylene or propylene.

DETAILED DESCRIPTION OF THE INVENTION

In accordance with the process of this invention, 2,6-dimethoxyphenol is reacted with a tertiary carbinol of the formula $R_1OH$, in which $R_1$ is adamantyl or —CR$_2$R$_3$R$_4$, wherein R$_2$ and R$_3$ independently are C$_1$-C$_6$ alkyl, and R$_4$ is C$_1$-C$_6$ alkyl, phenyl, cycloalkyl or adamantyl.

Examples of tertiary carbinols routinely incorporated in the reaction include tert.-butanol, 1,1-dimethyl-1-butanol, 1-methyl-1-ethyl-1-hexanol, 1,1-dimethyl-1-heptanol, 1,1-di-n-propyl-1-butanol, 1-methyl-1-n-butyl-1-phenylmethanol, 1,1-dimethyl-1-phenylmethanol, 1-methyl-1-ethyl-cyclohexylmethanol, 1,1-di-n-hexyl-1-phenylmethanol, 1,1-dimethyl-1-adamantylmethanol, and related carbinols. The reaction between the 2,6-dimethoxyphenol and the tertiary carbinol is carried out in the presence of an acid such as a sulfonic acid, for example methanesulfonic acid, sulfuric acid, para-toluenesulfonic acid and the like. An especially preferred acid is methanesulfonic acid. The alkylation reaction generally is carried out by commingling approximately equimolar quantities of the 2,6-dimethoxyphenol and the tertiary carbinol in the presence of an acid. The amount of acid utilized is not critical, and if desired, excessive amounts of acid can be utilized to the extent that such acid acts as solvent for the reaction in addition to being an alkylation catalyst. Alternatively the reaction can be carried out in a solvent such as dioxane, tetrahydrofuran, dimethyl sulfoxide, and the like, with about one molar quantity of acid being employed as catalyst. The reaction can be carried out at any temperature ranging from about 25° C. to about 80° C., and normally is conducted at about 50° C. The alkylation is usually substantially complete within about 1 to about 10 hours; however, longer reaction times can be used if desired. The product typically is isolated by simply removing the acid from the reaction mixture, for instance by adding the reaction mixture to a water immiscible solvent such as dichloromethane or ethyl acetate, and washing the solution several times with water, and if desired with an aqueous base such as a sodium bicarbonate solution in order to effect complete removal of any residual acid. Removal of the solvent from the organic solution then provides the product, which typically needs no further purification. While it would be expected that the position of alkylation of 2,6-dimethoxyphenol would be goverened by the ortho-para directing influences of the two methoxy groups, the above-described alkylation process surprisingly effects substantially predominantly substitution at the position meta to the two methoxy groups, thus providing almost exclusively a 1-hydroxy-2,6-dimethoxy-4-(tertiary alkyl)benzene. Such result is indeed surprising and represents a significant advance in the technology of producing 2,6-dimethoxy-4-(tertiary alkyl)phenols. A known process for preparing such compounds is that described in U.S. Pat. No. 2,888,503, which process comprises reacting 2,6-dimethoxyphenol with an alkenyl bromide to provide a 1-alkenoxy-2,6-dimethoxybenzene, which compound is then rearranged, generally by heating, to provide a 1-hydroxy-2,6-dimethoxy-4-alkenylbenzene, which upon hydrogenation affords the corresponding 1-hydroxy-2,6-dimethoxy-4-alkylbenzene.

The next step in preparing 5-(tertiary alkyl)-resorcinols according to this invention comprises reacting a 1-hydroxy-2,6-dimethoxy-4-(tertiary alkyl)benzene with a halogenated disubstituted phosphite to provide the corresponding 2,6-dimethoxy-4-(tertiary alkyl)phenyl disubstituted phosphate. Such reaction is quite general, as described for instance by Goldkamp et al. in *J. Med. Chem.*, 8 409 (1965), Kenner et al. in *J. Chem. Soc.*, 1955, 522, and Pelletier et al. in *J. Org. Chem.*, 23 131 (1958). The reaction is carried out by mixing approximately equimolar quantities of a 1-hydroxy-2,6-dimethoxy-4-(tertiary alkyl)benzene and a disubstituted phosphite in the presence of a carbon tetrahalide and an equimolar quantity of a base. Disubstituted phosphites commonly utilized in the process include dimethyl phosphite, diethyl phosphite, dipropyl phosphite, diphenyl phosphite, methyl phenyl phosphite, ethyl phenyl phosphite, 1,3-dioxo-2-phosphacyclopenta-2-oxide, and 1,4-dioxa-2-phosphacyclohexa-2-oxide. The disubstituted phosphite reacts with a carbon tetrahalide such as carbon tetrachloride, carbon tetrabromide or carbon tetraiodide, and a base such as triethylamine, pyridine, dimethylamine or aniline, to afford, in situ, a halogenated disubstituted phosphite, which then reacts with the 1-hydroxy-2,6-dimethoxy-4-(tertiary alkyl)benzene. The reaction normally is conducted in a suitable solvent such as chloroform, dichloromethane, carbon tetrachloride, or the like, and generally is carried out at a temperature ranging from about −20° C. to about 50° C., and usually is substantially complete within about 12 to about 24 hours. The products of such reaction, 2,6-dimethoxy-4-(tertiary alkyl)phenyl disubstituted phosphates, novel intermediates claimed herein, are readily isolated from the above-described reaction mixture by diluting the reaction mixture, if desired, with a water immiscible solvent such as dichloromethane or chloroform, and washing the solution several times with water, and if desired, with an aqueous sodium hydroxide solution and with an aqueous mineral acid such as hydrochloric or sulfuric acid. The organic solvent is then removed from the reaction mixture, for example by evaporation under reduced pressure, thus affording the desired 2,6-dimethoxy-4-(tertiary alkyl)phenyl disubstituted phosphate. Such product generally needs no further purification; however, if desired, the product can be further purified by routine procedures such as recrystallization and chromatography. Typical examples of 2,6-dimethoxy-4-(tertiary alkyl)phenyl disubstituted phosphates provided by this invention and routinely prepared according to the process of this invention include:

2,6-dimethoxy-4-(1,1-dimethylheptyl)phenyl diethyl phosphate;

2,6-dimethoxy-4-(1-ethyl-1-methylpentyl)phenyl dimethyl phosphate;

2,6-dimethoxy-4-(1,1-di-n-butylhexyl)phenyl dipropyl phosphate;

2,6-dimethoxy-4-(1-methyl-1-phenylbutyl)phenyl diphenyl phosphate;

2,6-dimethoxy-4-(adamantyl)phenyl methyl ethyl phosphate;

2,6-dimethoxy-4-(1,1-di-n-propyladamantylmethyl)-phenyl diethyl phosphate;

2,6-dimethoxy-4-(1-methyl-1-n-propylcyclohexylmethyl)phenyl ethyl phenyl phosphate;

2-[2,6-dimethoxy-4-(1,1-dimethylhexyl)phenoxy]-1,3-dioxa-2-phosphacyclopenta-2-oxide;

2,6-dimethoxy-4-(1,1-di-n-hexylheptyl)phenyl diethyl phosphate; and the like.

The 2,6-dimethoxy-4-(tertiary alkyl)phenyl disubstituted phosphates thus prepared are next reacted with an alkali metal such as sodium or lithium so as to effectively remove the disubstituted phosphate moiety to obtain the corresponding 1-(tertiary alkyl)-3,5-dimethoxybenzenes. Such reaction is general and is carried out according to the teachings of Goldkamp et al., Kanner et al., and Pelletier et al., ibid. Specifically, a solution of the above-referred to 2,6-dimethoxy-4-(tertiary alkyl)phenyl disubstituted phosphate dissolved in a solvent such as diethyl ether or tetrahydrofuran is added to a solution of an alkali metal such as sodium or potassium in liquid ammonia. A two molar quantity of the alkali metal is generally incorporated in the reaction; however, excessive quantities can be utilized if desired. The reaction generally is complete within about 2 to 10 hours, and the product is isolated by first decomposing any unreacted alkali metal, for instance by adding a aqueous solution of ammonium chloride to the reaction mixture, and then simply removing any reaction solvents, for instance by evaporation. If desired, the product can be dissolved in a water immiscible solvent such as diethyl ether and washed with an aqueous sodium hydroxide solution and with water. Removal of the organic solvent then provides the desired 1-(tertiary alkyl)-3,5-dimethoxybenzene which normally needs no further purification.

The next step in the instant process involves cleavage of the two methyl ether groups of the 1-(tertiary alkyl)-3,5-dimethoxybenzene by reaction with a demethylating agent to provide the corresponding 5-(tertiary alkyl)resorcinol. Such cleavage can be accomplished by simply heating the dimethoxy derivative in a mixture of pyridine hydrochloride. Such mixture is heated at reflux for a period of time ranging from about 2 to 10 hours, thus effecting cleavage of the two methyl ether groups. Alternatively, the 1-(tertiary alkyl)-3,5-dimethoxybenzene can be reacted with a boron trihalide such as boron tribromide or boron trichloride, or an aluminum halide such as aluminum bromide or aluminum chloride, thus effecting cleavage of the two methyl ether groups. Such reaction typically is carried out in a solvent such as dichloromethane or n-pentane, and generally is conducted at a reduced temperature ranging from about −80° C. to 25° C. The product, a 5-(tertiary alkyl)resorcinol, is isolated by evaporation of the solvent, and further purification can be accomplished by crystallization or chromatography. Cleavage of the two methyl ether groups can additionally be effected by reaction of the 1-(tertiary alkyl)-3,5-dimethoxybenzene with a mixture of hydrobromic acid in acetic acid.

As hereinbefore pointed out, the 5-(tertiary alkyl)resorcinols thus prepared in accordance with this invention are important intermediates in the preparation of useful drugs. For example, 5-(1,1-dimethylheptyl)resorcinol is utilized in the preparation of 1-hydroxy-3-(1,1-dimethylheptyl)-6,6a,7,8,9,10,10a-hexahydro-6,6-dimethyl-9H-benzo[b,d]pyran-9-one, which compound is extremely useful in the treatment of depression in humans, as described in U.S. Pat. Nos. 3,928,598, 3,944,673, and 3,953,603. Similarly, 5-(1,1-dimethylheptyl)resorcinol is required in the synthesis of 3-(1,1-dimethylheptyl)-6a,7,8,9,10,10a-hexahydro-6,6-dimethyl-6H-dibenzo[b,d]pyran-1,9-diol, which compound is useful as a blood-pressure lowering agent. It can thus be seen that a commercially feasible process for preparing 5-(tertiary alkyl)resorcinols in high yield is desirable. This invention provides such a process.

In order to illustrate more fully the operation of the invention, the following examples are provided by way of illustration.

EXAMPLE 1

1-Hydroxy-2,6-dimethoxy-4-(1,1-dimethylheptyl)benzene

A solution containing 15.4 g. of 1-hydroxy-2,6-dimethoxybenzene and 14.4 g. of 1,1-dimethyl-1-hydroxyheptane in 20 ml. of methanesulfonic acid was heated at 50° C. and stirred for three and one-half hours. The reaction mixture next was poured over 50 g. of ice, and the resulting aqueous solution was extracted several times with dichloromethane. The organic extracts were combined, washed with water and with saturated aqueous sodium bicarbonate solution, and dried. Removal of the solvent by evaporation under reduced pressure provided 27.4 g. of 1-hydroxy-2,6-dimethoxy-4-(1,1-dimethylheptyl)benzene as an oil.

nmr (CDCl$_3$):

$\delta$ 0.5–1.9 (m, 19H, 1,1-dimethylheptyl)

$\delta$ 3.9 — (s, 6H, OCH$_3$)

$\delta$ 6.58 — (s, 2H, aromatic)

The following compounds were prepared by reacting 1-hydroxy-2,6-dimethoxybenzene with the appropriate tertiary carbinol according to the procedure set forth above:

1-Hydroxy-2,6-dimethoxy-4-(1,1-dimethylbenzyl)benzene.

1-Hydroxy-2,6-dimethoxy-4-(1,1-dimethylcyclohexylmethyl)benzene.

1-Hydroxy-2,6-dimethoxy-4-(1-methyl-1-n-hexylbenzyl)benzene.

1-Hydroxy-2,6-dimethoxy-4-(1,1-dimethyl-adamantylmethyl)benzene.

1-Hydroxy-2,6-dimethoxy-4-adamantyl benzene.

EXAMPLE 2

2,6-Dimethoxy-4-(1,1-dimethylheptyl)phenyl diethyl phosphate

A solution of 35.9 g. of 1-hydroxy-2,6-dimethyl-4-(1,1-dimethylheptyl)benzene from Example 1 in 20 ml. of carbon tetrachloride containing 20.8 g. of diethyl phosphite was cooled to about 5° C. in an ice bath and stirred while 15.2 g. of triethylamine was added dropwise over one-half hour. The reaction mixture was then warmed to room temperature and was stirred for seventeen hours. The reaction mixture next was added to 50 ml. of dichloromethane and washed with water and with a dilute solution of aqueous sodium hydroxide. The organic solution was filtered, washed with 1N hydrochloric acid solution and with water, and dried. Removal of the solvant by evaporation under reduced pressure afforded a solid product which was then recrystallized from n-hexane to provide 37.0 g. of 2,6-dimethoxy-4-(1,1-dimethylheptyl)phenyl diethyl phosphate. M.P. 61°–67° C.

nmr (CDCl$_3$):

$\delta$ 6.55 (s, 2H, aromatic)

$\delta$ 4.30 (2 quartets, 4H, ethoxy methylenes)

$\delta$ 3.85 (s, 6H, OCH$_3$)

$\delta$ 1.4 (t, 6H, ethoxy methyls)

$\delta$ 1.25 (s, 6H, C(CH$_3$)$_2$)

According to the procedure set forth above, the following compounds were prepared by reacting the appropriate disubstituted phosphite, carbon tetrachloride, and triethylamine with the appropriate 1-hydroxy-2,6-dimethoxy-4-substituted benzene:

2,6-Dimethoxy-4-(1,1-dimethylbenzyl)phenyl diethyl phosphate.

2,6-Dimethoxy-4-(1,1-dimethylcyclohexylmethyl)-phenyl diethyl phosphate.
2,6-Dimethoxy-4-(1-methyl-1-n-hexyl-benzyl)phenyl diethyl phosphate.
2,6-Dimethoxy-4-(1,1-dimethyl-adamantylmethyl)-phenyl diethyl phosphate.
2,6-Dimethoxy-4-adamantylphenyl diethyl phosphate
2,6-Dimethoxy-4-(1,1-dimethylheptyl)phenyl dimethyl phosphate.

EXAMPLE 3

1-(1,1-Dimethylheptyl)-3,5-dimethoxybenzene

A solution of 36.5 g. of 2,6-dimethoxy-4-(1,1-dimethylheptyl)phenyl diethyl phosphate from Example 2 dissolved in 75 ml. of diethyl ether and 15 ml. of tetrahydrofuran was added dropwise over thirty minutes to a stirred solution of lithium metal in 200 ml. of liquid ammonia. The reaction mixture was stirred for one hour, after which time excess lithium metal was destroyed by addition to the reaction mixture of a solution of aqueous ammonium chloride. The reaction mixture was then added to 100 ml. of diethyl ether, and the excess ammonia solvent was allowed to evaporate. The ethereal solution was then washed with water and with aqueous sodium hydroxide, and dried. Removal of the solvent by evaporation under reduced pressure provided 22.1 g. of 1-(1,1-dimethylheptyl)-3,5-dimethoxybenzene as an oil.

nmr (CDCl$_3$):
$\delta$ 6.45 (d, 2H, C-2, C-6 aromatic)
$\delta$ 6.25 (t, 1H, C-4 aromatic)
$\delta$ 3.75 (s, 6H, OCH$_3$)
$\delta$ 1.25 (s, 6H, C(CH$_3$)$_2$)

Following the procedure set forth in Example 3, the respective 2,6-dimethoxy-4-substituted phenyl disubstituted phosphate was treated with lithium in ammonia to provide the following 1-substituted-3,5-dimethoxybenzenes.

1-(1,1-Dimethylbenzyl)-3,5-dimethoxybenzene.
1-(1,1-Dimethylcyclohexylmethyl)-3,5-dimethoxybenzene.
1-(1-Methyl-1-n-hexylbenzyl)-3,5-dimethoxybenzene.
1-(1,1-Dimethyl-adamantylmethyl)-3,5-dimethoxybenzene.
1-Adamantyl-3,5-dimethoxybenzene.

EXAMPLE 4

5-(1,1-dimethylheptyl)resorcinol

To a cold stirred solution of 62.5 g. of boron tribromide in 200 ml. of dichloromethane was added dropwise over one hour a solution of 26.4 g. of 1-(1,1-dimethylheptyl)-3,5-dimethoxybenzene from Example 3 dissolved in 100 ml. of dichloromethane. The reaction mixture was stirred at 0° C. for two hours, and then allowed to warm to room temperature, and then stirred for additional twelve hours. After cooling the reaction mixture again to 0° C., it was added slowly to 200 ml. of water. The organic layer was then separated, and the product was extracted therefrom into 2N sodium hydroxide solution. The aqueous alkaline solution was then acidified by the addition of 1N hydrochloric acid. The aqueous acid solution was then extracted several times with diethyl ether. The ethereal extracts were combined, washed with aqueous sodium chloride solution, and dried. The solvent was removed by evaporation under reduced pressure to afford 20.2 g. of 5-(1,1-dimethylheptyl)resorcinol. M.P. 97°-99° C.

nmr (CDCl$_3$):
$\delta$ 6.35 (d, 2H, aromatic)
$\delta$ 6.15 (t, 1H, aromatic)
$\delta$ 5.20 (broad s, 2H, OH)
$\delta$ 1.20 (s, 6H, C(CH$_3$)$_2$)
$\delta$ 1.8-0.5 (m, 13H, alkyl)

EXAMPLE 5

5-(1,1-dimethylheptyl)resorcinol

A mixture of 21.2 g. of 1-(1,1-dimethylheptyl)-3,5-dimethoxybenzene and 55.0 g. of pyridine hydrochloride was heated at reflux and stirred for 5½ hours. The reaction mixture then was cooled to room temperature and added to 150 ml. of water. The aqueous solution was extracted several times with diethyl ether, and the ethereal extracts were washed with water and dried. Removal of the solvent by evaporation under reduced pressure provided the product as a solid residue. The solid was recrystallized from 40 ml. of n-hexane to afford 13.0 g. of 5-(1,1-dimethylheptyl)resorcinol. M.P. 97°-99° C.

nmr (CDCl$_3$):
$\delta$ 6.35 (d, 2H, aromatic)
$\delta$ 6.15 (t, 1H, aromatic)
$\delta$ 5.2 (broad s, 2H, OH)
$\delta$ 1.20 (s, 6H, C(CH$_3$)$_2$)

EXAMPLE 6

5-(1,1-dimethylheptyl)resorcinol

A solution of 425 g. of 1-(1,1-dimethylheptyl)-3,5-dimethoxybenzene in 1700 ml. of glacial acetic acid containing 850 ml. of forty-eight percent aqueous hydrobromic acid was stirred and heated at reflux for 12 hours. The reaction mixture was cooled to room temperature and added to 6000 ml. of water. The aqueous reaction mixture was stirred while the product crystallized out of solution. Filtration of the mixture afforded 371 g. of 5-(1,1-dimethylheptyl)resorcinol. M.P. 93°-95° C.

Following the procedures set forth in Examples 4, 5 and 6, the respective 1-substituted-3,5-dimethoxybenzene was converted to the following resorcinol derivatives:

5-(1,1-Dimethylbenzyl)resorcinol M.P. 108°-110° C.
5-(1,1-Dimethylcyclohexylmethyl)resorcinol M.P. 145°-147° C.
5-(1-Methyl-1-n-hexylphenyl)resorcinol oil.
5-(1,1-Dimethyladamantylmethyl)resorcinol M.P. 125°-127° C.
5-Adamantylresorcinol M.P. 284°-285° C.

We claim:
1. A compound of the formula

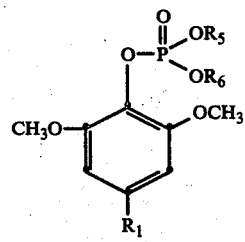

wherein:
R$_1$ is adamantyl or —CR$_2$R$_3$R$_4$, in which:
R$_2$ and R$_3$ independently are C$_1$-C$_6$ alkyl;

$R_4$ is $C_1$–$C_6$ alkyl, phenyl, cycloalkyl, or adamantyl, and $R_5$ and $R_6$ independently are $C_1$–$C_3$ alkyl or phenyl, or taken together are ethylene or proplylene.

2. The compound of claim 1 wherein $R_1$ is $CR_2R_3R_4$.

3. The compound of claim 2 wherein $R_4$ is $C_1$–$C_6$ alkyl.

4. The compound of claim 3 wherein $R_5$ and $R_6$ independently are $C_1$–$C_3$ alkyl.

5. The compound of claim 3 wherein $R_1$ is 1,1-dimethylheptyl.

6. The compound of claim 5, said compound being 2,6-dimethoxy-4-(1,1-dimethylheptyl)phenyl diethyl phosphate.

7. The compound of claim 5 wherein $R_5$ and $R_6$ independently are $C_1$–$C_3$ alkyl.

8. The compound of claim 5, said compound being 2,6-dimethoxy-4-(1,1-dimethylheptyl)phenyl dimethylphosphate.

9. The compound of claim 5 wherein $R_5$ and $R_6$, taken together are ethylene or propylene.

10. The compound of claim 5 wherein $R_5$ and $R_6$ independently are $C_1$–$C_3$ alkyl or phenyl.

* * * * *